(12) United States Patent
Ihatsu

(10) Patent No.: US 11,229,453 B2
(45) Date of Patent: Jan. 25, 2022

(54) TILT-CONTROLLED GRID

(71) Applicant: KONINKLIJKE PHILIPS N.V., Eindhoven (NL)

(72) Inventor: Mika Tapani Ihatsu, Gainesville, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 16/493,360

(22) PCT Filed: Mar. 13, 2018

(86) PCT No.: PCT/EP2018/056141
§ 371 (c)(1),
(2) Date: Sep. 12, 2019

(87) PCT Pub. No.: WO2018/167002
PCT Pub. Date: Sep. 20, 2018

(65) Prior Publication Data
US 2020/0129204 A1    Apr. 30, 2020

Related U.S. Application Data

(60) Provisional application No. 62/472,172, filed on Mar. 16, 2017.

(51) Int. Cl.
*A61B 17/34* (2006.01)
*A61B 10/02* (2006.01)
(Continued)

(52) U.S. Cl.
CPC ...... *A61B 17/3403* (2013.01); *A61B 10/0233* (2013.01); *A61B 2017/3409* (2013.01);
(Continued)

(58) Field of Classification Search
CPC ........ A61B 17/3403; A61B 2017/3409; A61B 2017/3411; A61B 90/10; A61B 90/11;
(Continued)

(56) References Cited

U.S. PATENT DOCUMENTS 4,899,756 A * 2/1990 Sonek .................. A61B 8/0833
600/461
5,931,786 A * 8/1999 Whitmore, III ..... A61B 8/4209
600/459
(Continued)

FOREIGN PATENT DOCUMENTS

WO    2016135595 A1    9/2016

OTHER PUBLICATIONS

International Search Report and Written Opinon From PCT/EP2018/056141 dated Jun. 7, 2018.

*Primary Examiner* — Darwin P Erezo
*Assistant Examiner* — Brigid K Byrd
(74) *Attorney, Agent, or Firm* — Sherry Austin

(57) ABSTRACT

An apparatus for controlling a needle guide includes a first lever, a second lever, a first cam and a second cam. The first cam is attached to and extends from the first lever to a housing under the needle guide. The second cam is attached to and extends from the second lever to the housing under the needle guide. At least one of the first cam and the second cam is configured to translate rotational movement from the
(Continued)

first lever and the second lever to both linear and rotational movement of the needle guide via the housing.

20 Claims, 12 Drawing Sheets

(51) Int. Cl.
  *A61B 34/20* (2016.01)
  *A61B 90/00* (2016.01)
(52) U.S. Cl.
  CPC .............. *A61B 2017/3411* (2013.01); *A61B 2034/2051* (2016.02); *A61B 2090/374* (2016.02)
(58) Field of Classification Search
  CPC .......... A61B 2090/101; A61B 10/0233–0283; A61B 2034/301; A61B 90/50; A61B 90/57
  See application file for complete search history.

(56) References Cited

U.S. PATENT DOCUMENTS

| | | | |
|---|---|---|---|
| 6,221,030 B1* | 4/2001 | Avaltroni | A61B 10/0266 600/567 |
| 6,248,101 B1 | 6/2001 | Whitmore, III | |
| 6,398,711 B1 | 6/2002 | Green et al. | |
| 6,554,759 B2 | 4/2003 | Fontayne et al. | |
| 8,162,884 B2 | 4/2012 | Van Hooft | |
| 8,764,619 B2 | 7/2014 | Pitman | |
| 2002/0038071 A1 | 3/2002 | Fontayne et al. | |
| 2002/0042607 A1* | 4/2002 | Palmer | A61B 17/3417 606/1 |
| 2002/0177807 A1* | 11/2002 | Huitema | A61N 5/1007 604/116 |
| 2006/0015085 A1* | 1/2006 | Bates | A61B 17/3478 604/508 |
| 2006/0016006 A1* | 1/2006 | Whitmore, III | A61B 6/0442 5/601 |
| 2012/0283563 A1 | 11/2012 | Moore et al. | |
| 2015/0146951 A1 | 5/2015 | Zagorchev et al. | |
| 2019/0175214 A1* | 6/2019 | Wood | A61B 8/4209 |
| 2021/0016104 A1* | 1/2021 | Cavanaugh | A61N 5/1007 |

* cited by examiner

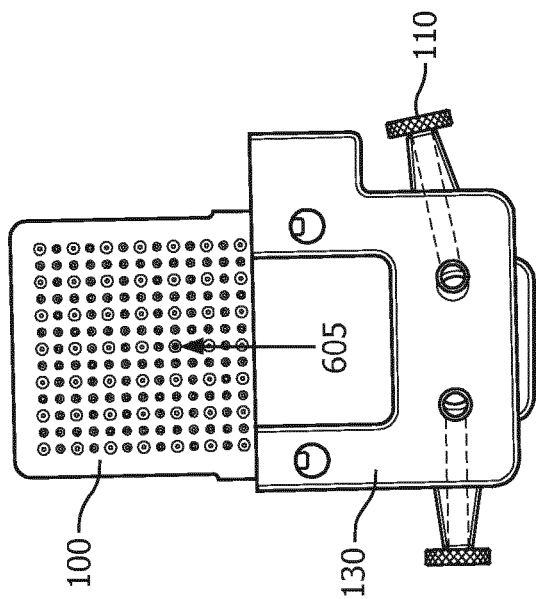
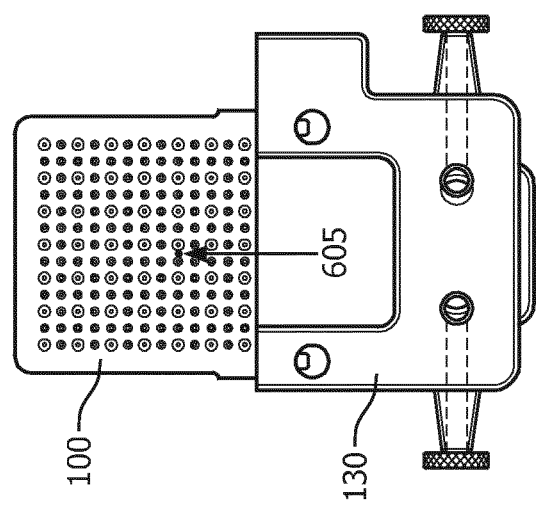
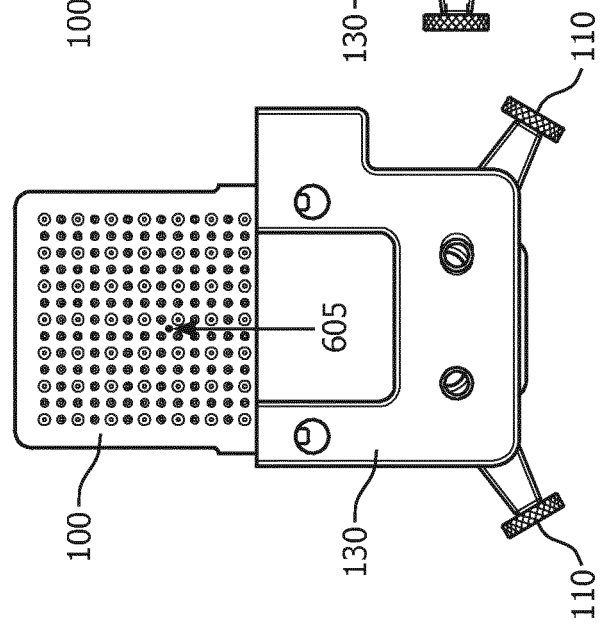
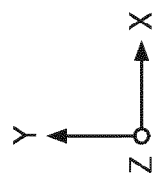

TILT-CONTROLLED GRID

CROSS REFERENCE TO RELATED APPLICATIONS

This application is a U.S. national phase application of International Application No. PCT/EP2018/056141 filed on Mar. 13, 2018, which claims the benefit of U.S. Provisional Application Ser. No. 62/472,172 filed on Mar. 16, 2017 and is incorporated herein by reference.

BACKGROUND

A transperineal stepper uses a grid plate to drive a biopsy needle through an intended location of the perineum (i.e., the area between the anus and the scrotum or vulva). The grid plate has a grid pattern of holes for the biopsy needle. To reach all possible intended locations, the grid plate must be movable. Movement of the grid plate is limited to X and Y directions that are orthogonal to one another. The grid has to be movable in each of the X and Y directions individually to reach the intended location. For example, 5 mm hole spacing needs at least 2.5 mm (millimeters) movement in each of the X and Y directions to reach each possible intended location. Traditionally, driving screws and linear sliders are used to accomplish the individual X movement and Y movement. The driving screws and linear sliders are placed in an area below the grid plate, and the grid plate is placed against a patient. The driving screw and linear slider for the X direction operate independently of the driving screw and linear slider for the Y direction.

The driving screws are located in the transperineal stepper. Due to the design and placement of components such as the driving screws, there is typically not much room for fingers to manipulate the driving screws. Additionally, biological residue tends to fall right to the driving screws and linear sliders since the driving screws and linear sliders are below the grid plate. Cleaning the biological residue can be difficult given the tight space in the area of the driving screws below the grid plate. If not cleaned, the biological residue can cause jamming in the driving screws and the linear sliders. Moreover, driving screws only slowly move the linear sliders, and many full screw rotations may be necessary to reach an intended location even though the movement is no more than a few millimeters. Finally, because the X and Y sliders must work independently, the design of the driving screws and linear sliders for the X movement and Y movement can be complicated.

SUMMARY

According to an aspect of the present disclosure, an apparatus is provided for controlling a needle guide. The apparatus includes a first lever, a second lever, a first cam and a second cam. The first cam is attached to and extends from the first lever to a housing under the needle guide. The second cam is attached to and extends from the second lever to the housing under the needle guide. At least one of the first cam and the second cam is configured to translate rotational movement from the first lever and the second lever to both linear and rotational movement of the needle guide via the housing.

According to another aspect of the present disclosure, the apparatus also includes a first device and a second device. The first device is integrated with the first cam to convey the rotational movement from the first lever substantially horizontally to the housing. The second device is integrated with the second cam to convey the rotational movement from the second lever substantially horizontally to the housing.

According to still another aspect of the present disclosure, the housing includes a first gear and a second gear. The first gear is configured to translate rotational movement from the first cam to linear movement via the housing. The second gear is configured to translate rotational movement from the second cam to linear movement via the housing.

According to yet another aspect of the present disclosure, the needle guide is a grid plate. When the first lever and the second lever are moved together, the grid plate moves substantially vertically.

According to another aspect of the present disclosure, the needle guide is a grid plate. When the first lever is moved and the second lever is maintained stationary, the grid plate is held in place about a pivot while being rotated about the pivot.

According to still another aspect of the present disclosure, the rotational movement of the needle guide tilts the needle guide around an axis.

According to yet another aspect of the present disclosure, the axis is moved when at least one of the first cam and the second cam translates movement from at least one of the first lever and second lever to the linear movement of the needle guide via the housing.

According to another aspect of the present disclosure, the apparatus includes a transperineal stepper.

According to still another aspect of the present disclosure, the apparatus includes the needle guide, and the needle guide is a grid plate.

According to yet another aspect of the present disclosure, the grid plate is guided by manipulating at least one of the first lever and second lever so that one of a plurality of holes in the grid plate is manipulated to align with a target location.

According to another aspect of the present disclosure, the first lever and the second lever are provided at a horizontal offset from the housing under the needle guide.

According to still another aspect of the present disclosure, rotation of the first lever about a first axis by less than 180 degrees and rotation of the second lever about a second axis by less than 180 degrees produces vertical movement of the grid plate in a range less than 25 millimeters.

According to yet another aspect of the present disclosure, rotation of the first lever about a first axis while the second lever is maintained stationary holds the grid in place about a pivot while the needle guide is rotated about the pivot by the first lever.

According to another aspect of the present disclosure, the apparatus includes an imaging device that captures data used to produce an image of a target location in real time. The imaging device may be, for example, an ultrasound machine or system, or another similar kind of device that uses electromagnetism to image characteristics of a subject.

According to still another aspect of the present disclosure, movement of at least one of the first lever and the second lever about an axis is diminished in linear translation to the grid. Vertical and rotational movement of the needle guide is magnified in the image of the target location in real time.

According to an aspect of the present disclosure, an apparatus for controlling a needle guide includes a housing, a first cam, a second cam, a first lever and a second lever. The housing is under the needle guide. The first cam is configured to translate rotational movement to linear movement via the housing. The first cam includes a first central axis therethrough and a first peg that directly contacts the housing. The second cam is configured to translate rotational movement to linear movement via the housing. The second cam includes a second central axis therethrough and a second peg that directly contacts the housing. The first lever is attached to the first cam at a horizontal offset from the housing and is configured to rotate the first cam about the first central axis to convey the rotational movement of the first cam. The second lever is attached to the second cam at a horizontal offset from the housing and is configured to rotate the second cam about the second central axis to convey the rotational movement of the second cam. At least one of the first cam and the second cam is configured to translate rotational movement from the first lever and the second lever to both linear and rotational movement of the needle guide via the housing.

According to another aspect of the present disclosure, the first central axis and second central axis are parallel lines.

According to another aspect of the present disclosure, the first cam is fixed in place relative to the housing so as to be rotated by the first lever. The second cam is linearly movable relative to the housing and configured to be rotated by the second lever.

According to another aspect of the invention, the apparatus includes a centralizer part to fix the distance of levers and a pin or pins centrally and limit the grid plate's horizontal movement, but let the grid plate travel up-down and rotate.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIGS. 8A-8C are front views showing lift and tilt operations for a grid plate, in accordance with a representative embodiment.

DETAILED DESCRIPTION

Figure 1:
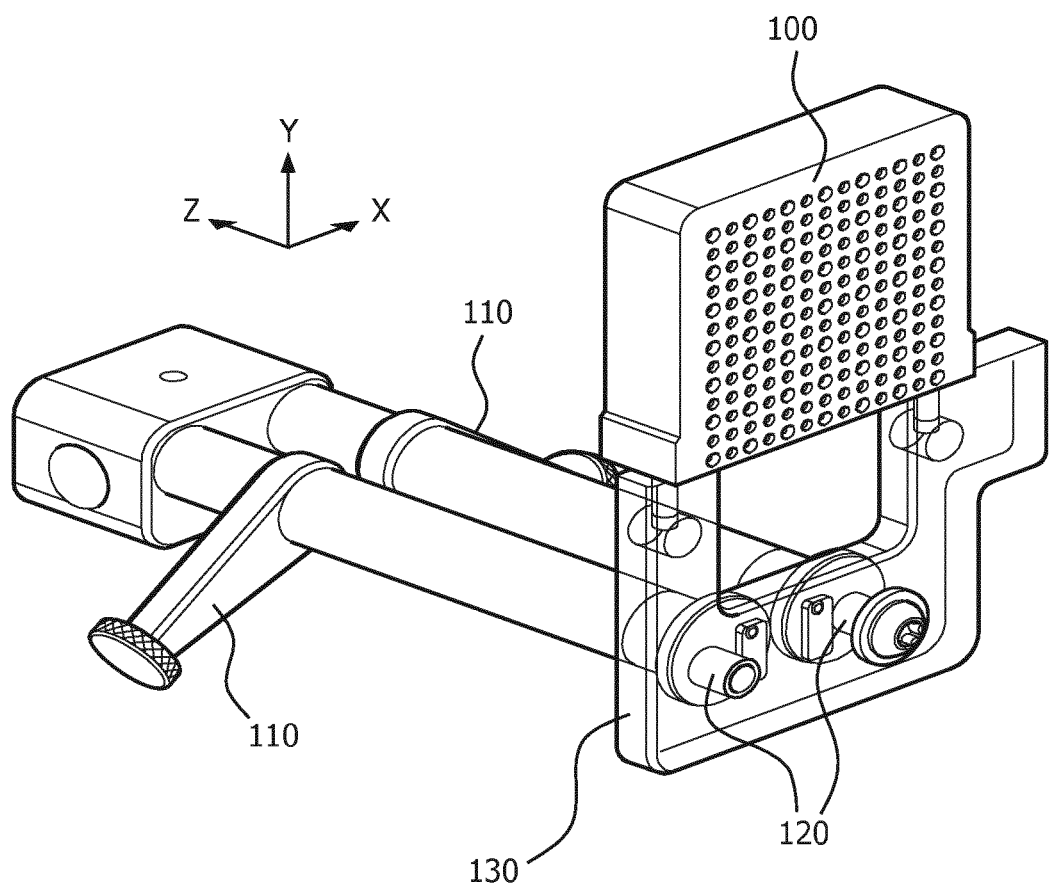
FIG. 1 is a perspective view of a system for a tilt-controlled grid, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

FIG. 1 is a perspective view of a system for a tilt-controlled grid, in accordance with a representative embodiment. In FIG. 1, the system for a tilt-controlled grid includes two levers 110 and two cams 120. A grid body 130 may be provided as part of the system for a tilt-controlled grid or may be provided with the grid plate 100 or may be provided separately. Thus, in an embodiment, the system for a tilt-controlled grid includes the two levers 110, two cams 120, and the grid body 130. One cam 120 (i.e., a first cam) is attached to and extends from one lever 110 (i.e., a first lever) to the grid body 130 under the grid plate 100. The other cam 120 (i.e., a second cam) is attached to and extends from the other lever 110 (i.e., a second lever) to the grid body 130 under the grid plate 100. As shown in FIG. 1, the levers 110 are provided at a substantial horizontal offset from the grid body 130, such as eight or twelve inches. Additionally, the two cams 120 may have axes that are parallel lines, and may both lie in the same horizontal plane. Even if not exactly parallel, the two cams 120 will have axes that are substantially parallel, and may both be very close to horizontal.

The grid body 130 may be a housing that houses movable components (not shown) internally. Movable components convey motion vertically upward to move the grid plate 100 vertically or to tilt the grid plate 100 in a movement that is both vertical and horizontal. The grid plate 100 in FIG. 1 is a needle guide that guides needles precisely where intended in a procedure.

A baseline coordinate system is shown for FIG. 1, wherein the X direction may be considered width, the Y direction may be considered height, and the Z direction may be considered depth. The two levers 110 are used to rotate corresponding cams 120, and the rotation of the cams 120 is translated into vertical movement of paired components in the grid body 130. The rotation of the cams 120 may be rotation of the outermost portion shown in FIG. 1, but is more typically rotation of, for example, a linear screw that is an internal component of the cams 120. The vertical movement of components in the grid body 130 can be commensurate (equivalent) and simultaneous, so that the grid body 130 moves vertically at the same time. Linear screws internal to the cams 120 may be individual devices that are integrated with each cam 120 and that convey rotational movement from the levers 110 horizontally through the cams 120 to the grid body 130.

Although linear screws internal to the cams 120 are described above as individual devices integrated with each cam, such individual devices do not have to be linear screws, and instead may be, for example, a spring load break pad. Any similar alternative device that conveys rotation by friction may be used, particularly so long as the rotation (i.e., from the first lever and the second lever) is not conveyed to the housing. In other words, an alternative device may work so long as the alternative device conveys rotation from the lever to friction without ultimately rotating the housing.

In an embodiment, the components in the grid body 130 are gears. The gears within the grid body 130 can be configured to translate movement (e.g., rotational movement) from the cams 120 to linear movement (i.e., vertical movement) through the grid body 130. The grid body 130 may be a housing that houses gears as well as other components. The internal components within the grid body 130 may be provided in pairs, so that one of a pair of component(s) translates movement from one cam 120, and the other of the pair of component(s) translates movement from the other cam 120. The pairs of component(s) of gears and other components in the grid body 130 may result in vertical movement along two parallel vertical lines.

In another embodiment, the two levers 110 do not rotate cams 120 or components within the cams 120. Instead, the levers 110 may be used to manipulate a pump or other mechanism to translate and convey motion through the cams 120 to the grid body 130.

The vertical movement of components in the grid body 130 can also be unitary where only one of the paired components is driven, or can be uneven where the paired components are driven at different rates and by different total amounts. If the vertical movement is unitary, the still component of the paired components forms a stationary axis about which the grid plate 100 will rotate. If the vertical movement is merely uneven, one of the paired components forms a floating axis about which the grid plate 100 will rotate. In either event, when the grid plate 100 is driven to rotate by vertical movement of one or more components in the grid body 130, the movement of the grid plate 100 can be either linear in the Y direction, or rotational about a fixed axis in the X and Y plane, or both linear in the Y direction and rotational about a moving axis in the X and Y plane.

In FIG. 1, the grid plate 100 is shown to include an array of holes. The holes are needle guides through which a needle can be placed. Although in FIG. 1 the grid plate 100 may appear to be a simple device, the grid plate 100 can be used in conjunction with other medical equipment for medical procedures that require extraordinarily precise control of, for example needles. As set forth in the initial portion of this disclosure, a procedure may be performed in the area of the perineum (i.e., the area between the anus and the scrotum or vulva), and a transperineal stepper may be used with the grid plate 100 to drive a biopsy needle through an intended location of the perineum.

Figure 2:
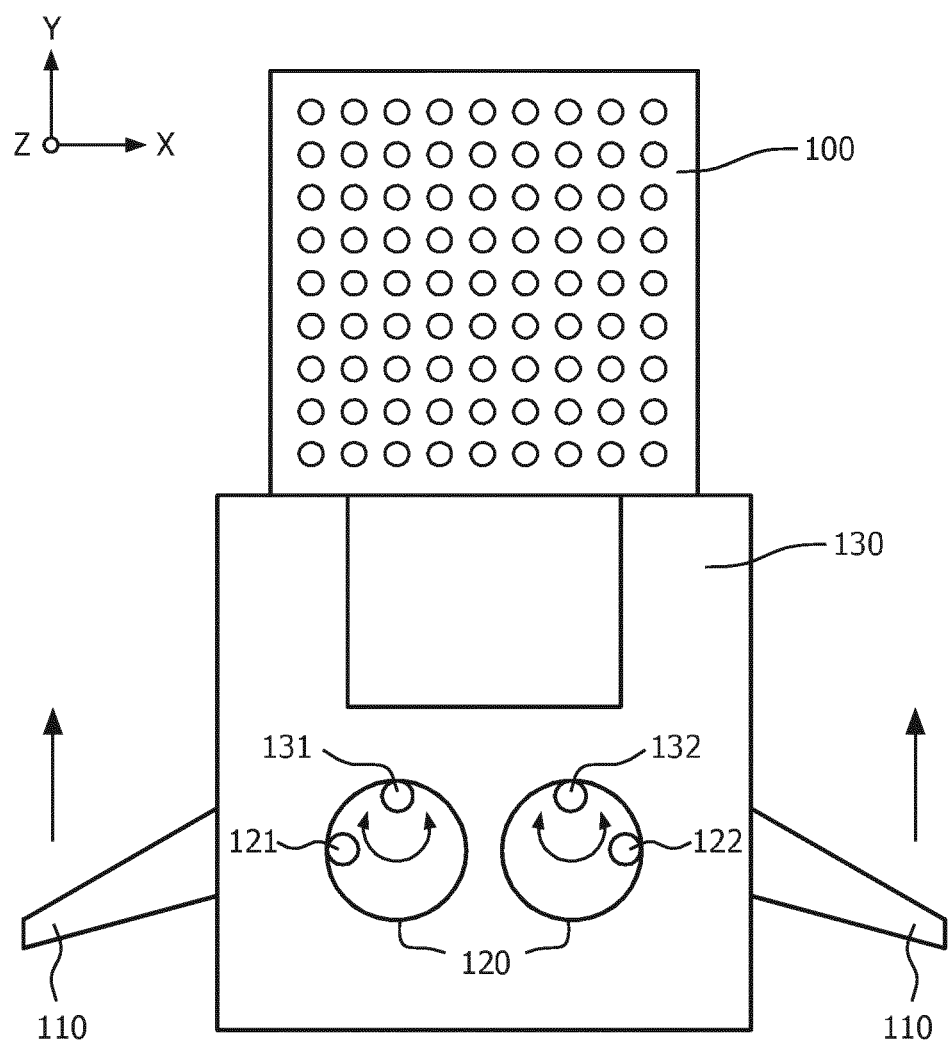
FIG. 2 is a front view of a system for a tilt-controlled grid, in accordance with a representative embodiment.

FIG. 2 is a front view of a system for a tilt-controlled grid, in accordance with a representative embodiment. In FIG. 2, arrows point up to show the direction in which the levers 110 are to be moved. The grid body 130 is lifted when both levers 1 10 are moved equally together. The grid body 130 is lifted and rotates when one lever 1 10 is moved less than the other lever 110, such that a floating axis is formed about which the grid body 130 is rotated. The grid body 130 is just rotated when one lever 110 remains stationary to form an axis while the other lever 1 10 drives the grid plate 100 to rotate about the axis.

In the front view of FIG. 2, each cam 120 is shown to include two small circles. The circles denote pegs 121, 122 and stoppers 131, 132 formed on the front of each cam 120. The pegs 121, 122 are formed on or with the cams 120, and are used to drive the internal components of the grid body 130 that are driven vertically by rotation of the cams 120. The stoppers 131, 132 are formed as part of the grid body 130, and stop the rotation of the cams 120 when the pegs 121, 122 are rotated up to the stoppers 131, 132.

As can be seen from the view in FIG. 2, the levers 110 can rotate no more than 180 degrees, and are more likely limited to motion through perhaps 120 degrees. The movement in the rotation of the levers 110 may be magnified in comparison to the slight incremental movement of the grid plate 100. For example, rotation of one lever 110 by less than 180 degrees and rotation of the other lever 110 by less than 180 degrees may translate into vertical movement of the grid plate 100 in a range less than 25 millimeters.

As described above, simultaneous and equivalent rotation of the levers 110 by less than 180 degrees produces vertical movement of the grid plate 100 in a range less than 25 millimeters, such as between 1 and 10 millimeters. As an example, rotation of each lever 110 by 60 degrees may produce vertical movement of the grid plate 100 between 1 and 10 millimeters. For practical purposes, the levers 110 may only be designed to move up to 120 degrees, and the grid plate 100 may be restricted from moving more than 25 mm horizontally and 10 mm vertically. The full effective rotation of the cams 120 may be 180 degrees, and the range of movement of the grid plate 100 may then depend on the size of the cams 120.

Figure 3A:
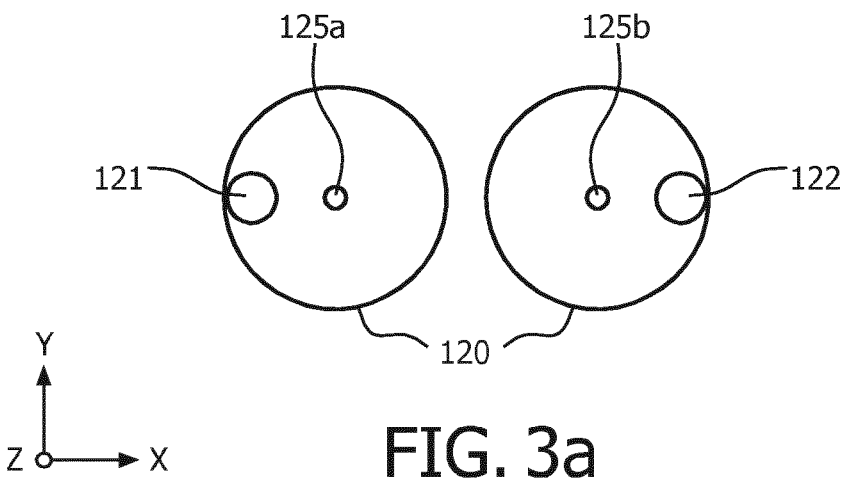
FIGS. 3A-3C are detailed front views of cams used in a system for a tilt-controlled grid, in accordance with a representative embodiment.
Figure 3B:
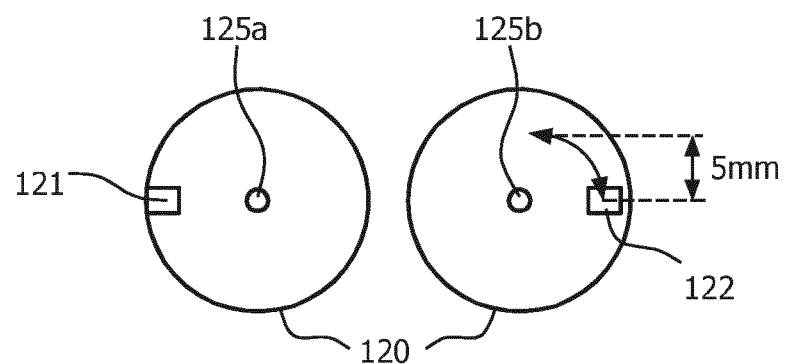
Figure 3C:
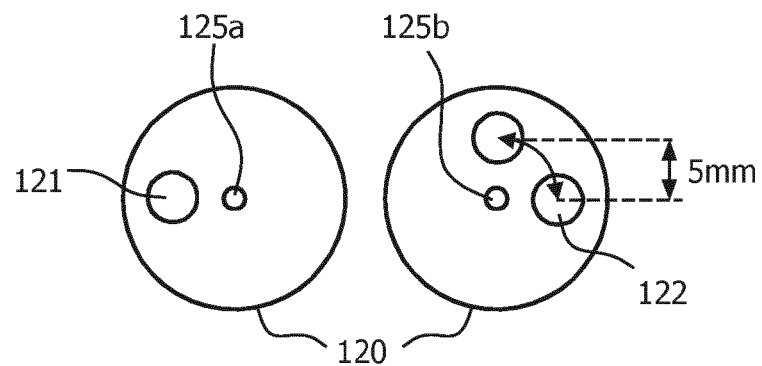

FIGS. 3A-3C are detailed front views of cams used in a system for a tilt-controlled grid, in accordance with a representative embodiment. In FIG. 3A, the two cams 120 are shown with corresponding pegs 121, 122. Each cam 120 has a corresponding axis 125a, 125b. The peg 121 rotates with one cam 120 about axis 125a. The peg 122 rotates with the other cam 120 about axis 125b. The rotation of the cams 120 stops when the pegs 121, 122 are stopped by the stoppers 131, 132 on the grid body 130.

In FIG. 3B, square pegs 121, 122 are used in comparison to round pegs 121, 122 in FIG. 3A. Additionally, an absolute vertical movement of 5 millimeters is shown as the difference between the vertical level of each axis 125a, 125b and a maximum vertical displacement.

In FIG. 3C, the pegs 121, 122 are shown to be placed within the perimeters of the cams 120, rather than up to the perimeters of the cams 120 as in FIGS. 3A and 3B. Additionally, the relative rotation of peg 122 about axis 125b is shown for the cam 120 on the right in FIG. 3B.

Figure 4:
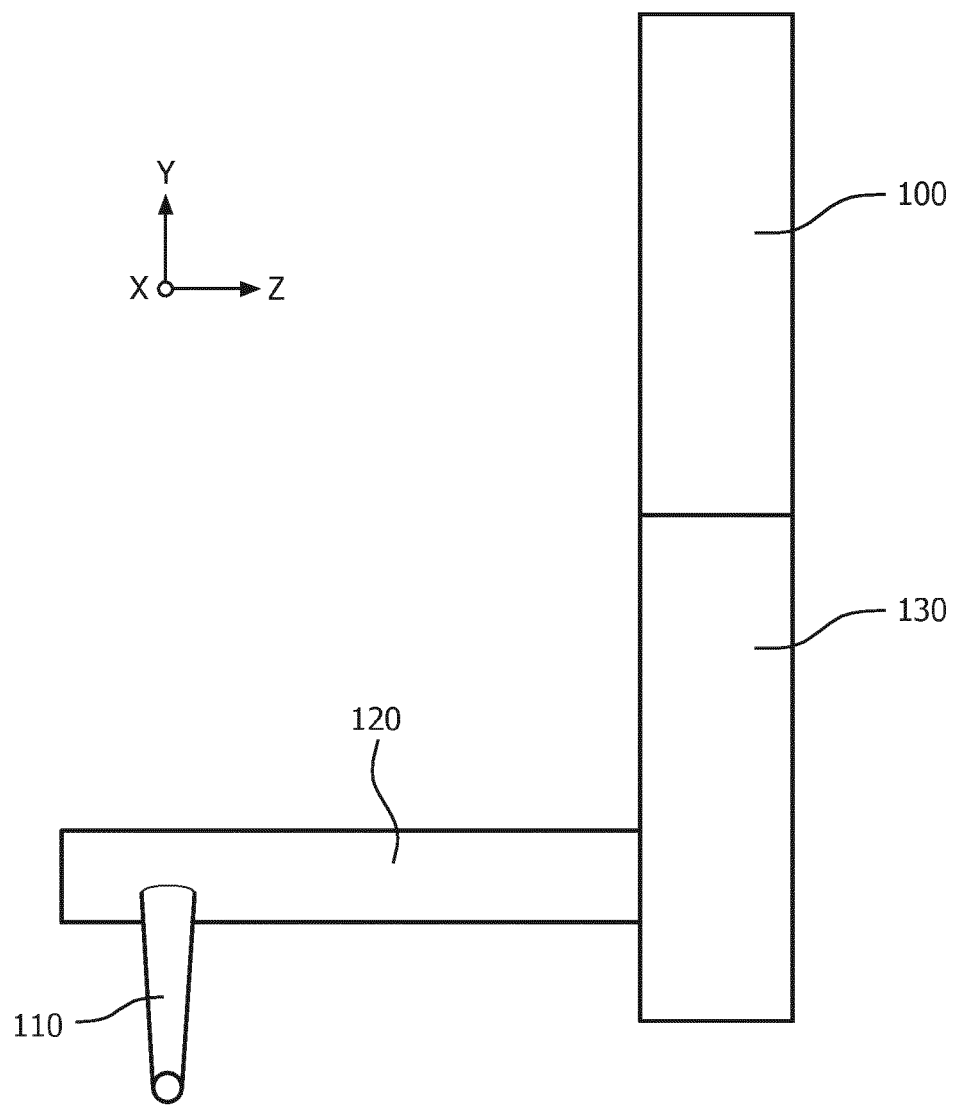
FIG. 4 is a side view of a system for a tilt-controlled grid, in accordance with a representative embodiment.

FIG. 4 is a side view of a system for a tilt-controlled grid, in accordance with a representative embodiment. In FIG. 4, the grid plate 100 is shown to have the same depth as the grid body 130. This is not absolutely required, however, and the grid body 130 may be substantially wider than the grid plate 100 or substantially narrower than the grid plate 100. Additionally, since FIG. 4 is a side view, only one cam 120 and one lever 110 are shown. The lever 110 appears to be disposed straight down relative to the cam 120, but this is a visual distortion insofar as the lever 110 is provided at a non-vertical angle in the XY plane at a default (starting) position or when rotating the cam 120.

In FIG. 4 and other embodiments, the lever 110 is shown at a position. Depending on the mechanisms used to translate rotational movement of the lever 110 into movement through the cam 120, the lever 110 may have a default position to which it returns or the lever 110 may remain in whatever position it is placed in last by an operator. The lever 110 may remain stationary in a last position when, for example, a linear screw mechanism is used within the cam 120 to translate and convey rotational movement of the lever 110 into vertical movement (i.e., up/down) in the grid body 130. However, in embodiments using a pump within the cam 120, or using a lever 110 that has a heavy weight, the lever 110 may be designed to return to the same position after each use.

Figure 5:
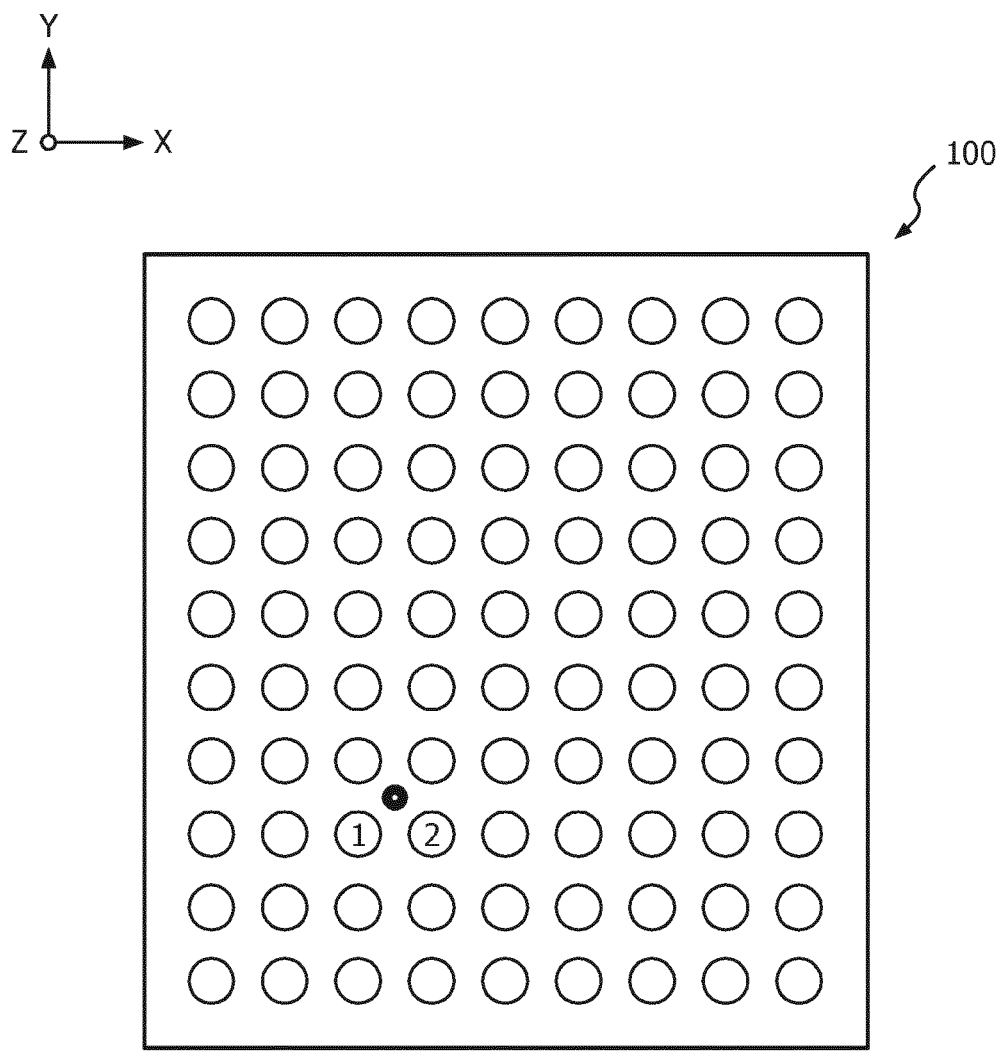
FIG. 5 is a front view of a grid plate, in accordance with a representative embodiment.

FIG. 5 is a front view of a grid plate, in accordance with a representative embodiment. In FIG. 5, two of the holes in grid plate 100 are labeled "1" and "2", and they are placed near a darkened marker that marks a corresponding location on the surface of a subject who will undergo a procedure involving a needle. That is, one of the holes labeled "1" and "2" must be placed over the darkened marker.

Figure 6:
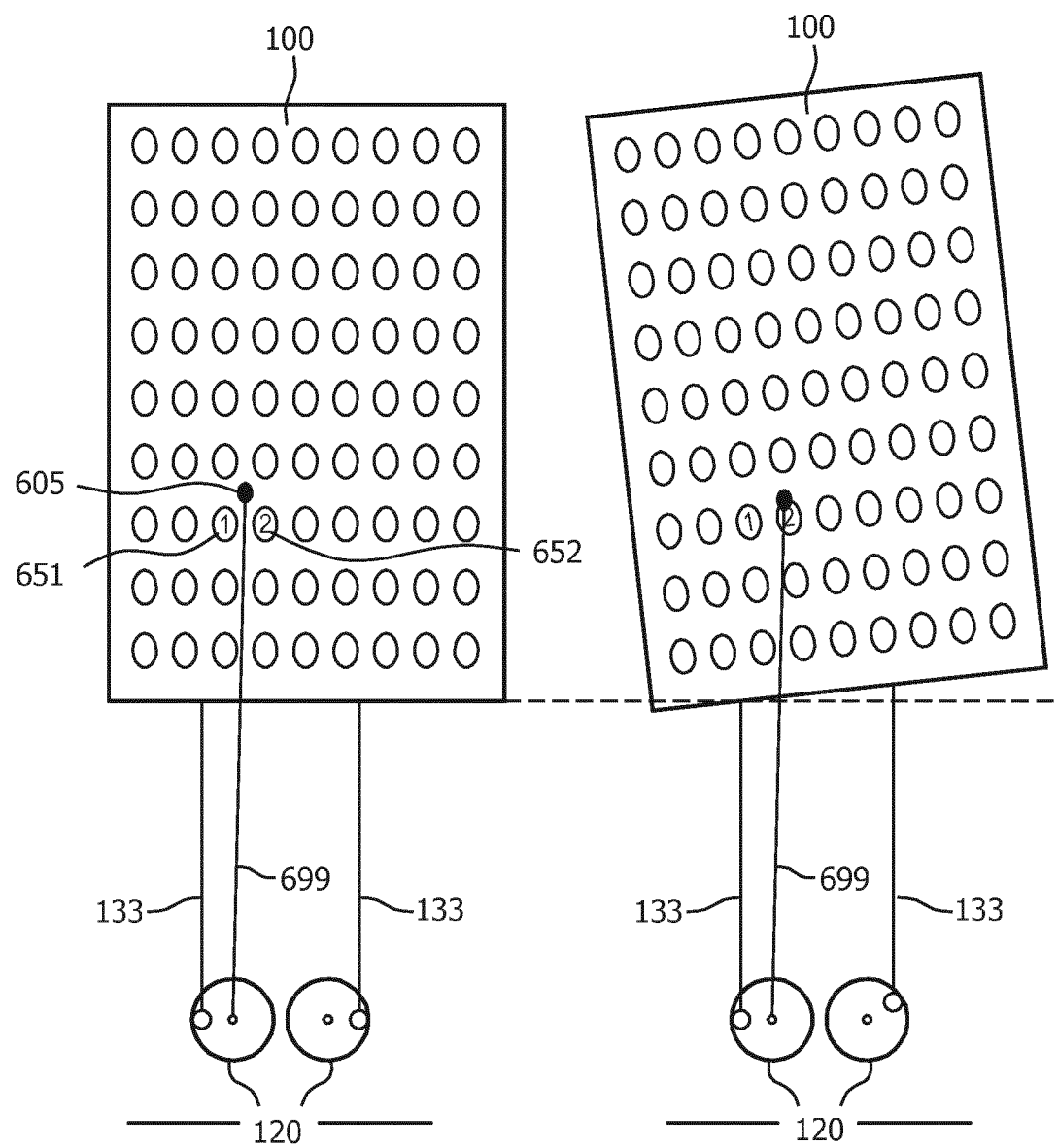
FIG. 6 is another front view showing a tilt operation for a grid plate, in accordance with a representative embodiment.

FIG. 6 is another front view showing a tilt operation for a grid plate, in accordance with a representative embodiment. In FIG. 6, the target location 605 for the tilted grid plate 100 is designated by a darkened spot. A first prospect hole 651 is labeled with a "1", and a second prospect hole 652 is labeled with a "2". An on-paper measurement stick 699 is shown superimposed on the tilted grid plate 100, so as to reflect where the target location is after the grid plate 100 is tilted on the right. As shown, after the grid plate 100 is tilted on the right using the top of a conveyance mechanism 133 of the grid body 130 as an axis, the second prospect hole 652 labeled "2" appears over the target location 605, such that the target location 605 is not labeled on the right. The conveyance mechanism 133 may be an internal component of the grid body 130, and an uppermost point of each conveyance mechanism 133 is a contact point that contacts the grid plate 100.

As can be seen in FIG. 6, the grid plate 100 is tilted above an axis formed by the uppermost point of the conveyance mechanism 133 where the conveyance mechanism 133 contacts the grid plate 100. The axis will be defined by whichever conveyance mechanism 133 is lower, such that the grid plate 100 will be rotated by movement of the other (higher) conveyance mechanism 133 higher. The conveyance mechanisms 133 may be, for example, a rigid rod that moves vertically with the rotation of a pin on a cam 20. The rotation occurs due to a component such as a conveyance mechanism 133 on one side of the grid body 130 moving more than a corresponding component (conveyance mechanism 133) on the other side of the grid body 130. In turn, the conveyance mechanisms 133 in the grid body 130 are moved by the cams 120, which are in turn moved by levers 110. Thus, when one lever 110 is moved more than another, the grid plate 100 tilts. If one lever 110 is not moved at all, a stationary axis will be used as the pivot. If one lever 110 is moved more than the other, but both levers 110 are moved, than a movable axis will be used as the pivot.

Figure 7:
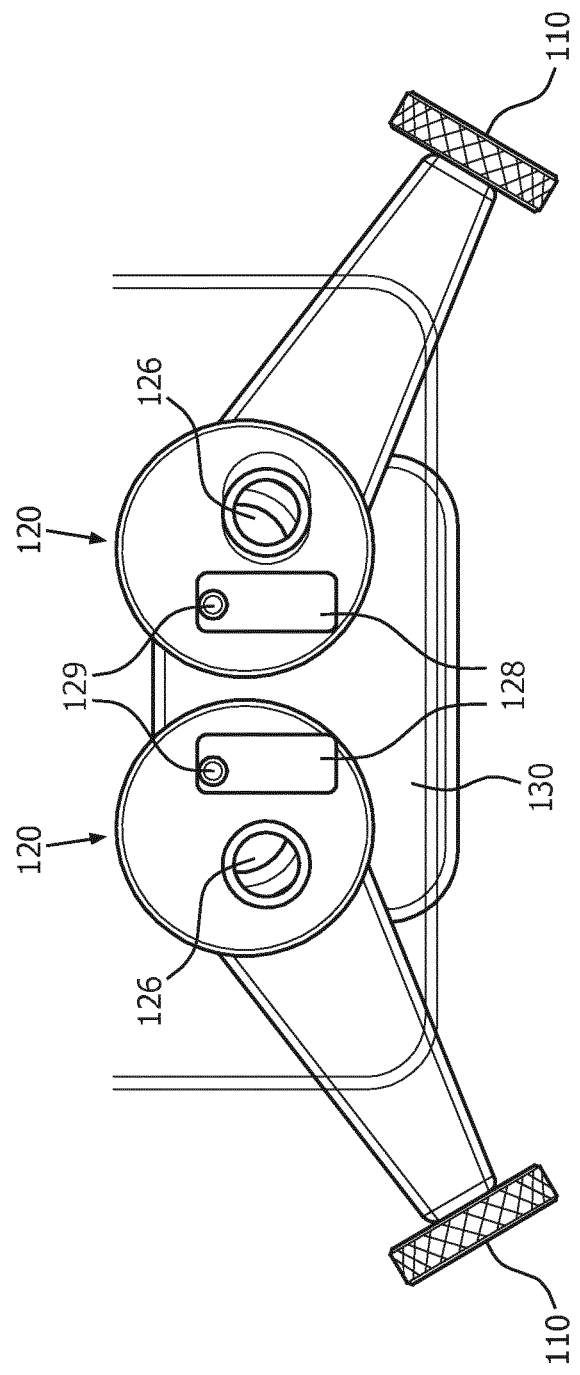
FIG. 7 is a front view of cams used in a system for a tilt-controlled grid, in accordance with a representative embodiment.

FIG. 7 is a front view of cams used in a system for a tilt-controlled grid, in accordance with a representative embodiment. In FIG. 7, two levers 110 are shown on left and right sides of a grid body 130. Two cams 120 are shown, each attached to a different lever 110, and both jutting from and attached to the grid body 130.

In FIG. 7, holes 126 pass entirely through each cam 120. The holes 126 represent screw holes for a screw internal to the cams 120. The screws are a representative mechanism to convey movement from the turning of the levers 110 to the vertical motion conveyed in the grid body 130 to the grid plate 100. The screws in the holes 126 claim the grid body 130 to the cams 120. The holes 126 in FIG. 7 may be large enough to allow an operator to insert a finger or tool (as on the right in FIG. 7). Alternatively, the holes 126 may be smaller in diameter, and may snugly fit around the screws or any other mechanism used to convey the movement from the levers 110 (as on the left in FIG. 7). In an embodiment, the holes 126 may not exist at all.

Additionally, in FIG. 7, each cam 120 is provided with a limiting pin 129 on a plate 128. The limiting pins 129 limit the movement of the cams 120 when the pegs 121, 122 hit the limiting pins 129 during rotation of the levers 110. The limiting pins 129 may be attached to, integrated with, integral to, part of, or otherwise fixedly attached to the cams 120. The limiting pins 129 are affixed to the cams 120 by the plates 128 when the plates 128 are affixed to the cams 120.

FIGS. 8A-8C are front views showing lift and tilt operations for a grid plate with target location 605, in accordance with a representative embodiment. In FIG. 8A, a grid plate 100 is shown on a grid body 130. Two levers 110 are shown in a default position. In FIG. 8B, the two levers 110 are lifted by the same amount, and the grid plate 100 is raised straight up without tilting. In FIG. 8C, one lever 110 is lifted more than the other, and the grid plate 100 tilts to the left about an axis formed on the lower left since the lever 110 on the right is lifted more.

In FIG. 8B the grid plate 100 is shown lifted straight up when the levers 110 are lifted up by equal amounts. The movement up would be movement only in the Y direction. On the other hand, while not absolutely necessary for any particular embodiment described herein, it may be that movement solely in the X direction is not possible. That is, while movement straight up can be accomplished by lifting both levers 110 equally, there is not an equal capacity for movement only to the left or right in the embodiment of FIG. 8 and possibly other embodiments. Rather, it may be that movement to the left or right is only accomplished by the tilting as shown in, for example, FIG. 8C, which also includes a vertical component.

Figure 9:
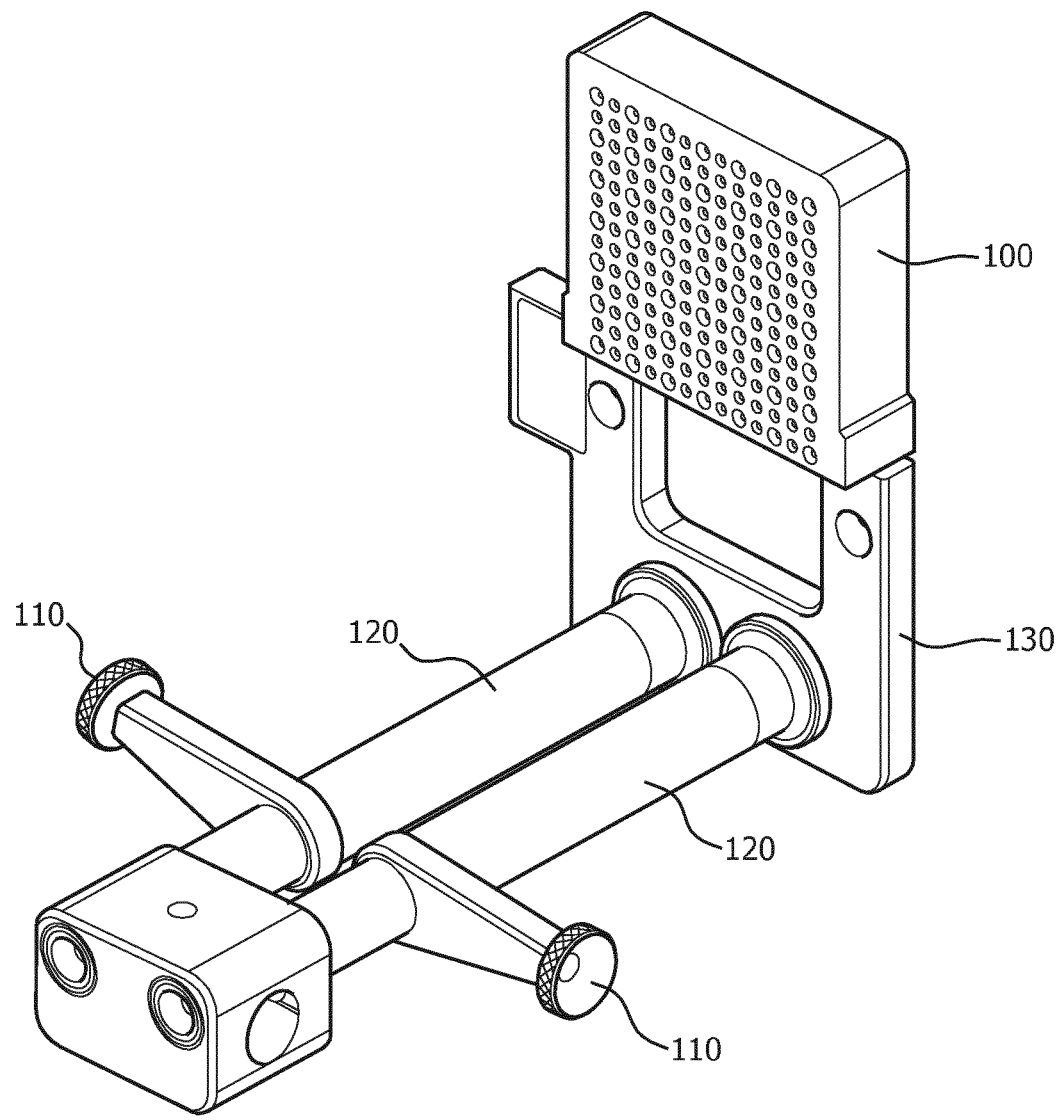
FIG. 9 is a perspective view showing a system for a tilt-controlled grid, in accordance with a representative embodiment.

FIG. 9 is a perspective view showing a system for a tilt-controlled grid, in accordance with a representative embodiment. As shown in FIG. 9, the levers 110 are placed away from the grid body 130. For example, the levers 110 may be placed 10-30 inches away from the grid body 130. This ensures that an operator operating the levers 110 has room to maneuver hands without interference from the grid body 130. This also ensures that biologic material that falls from the grid plate 100 does not get caught up in the area where the operator's hands have to maneuver, which in turn makes the system for a tilt-controlled grid in FIG. 9 relatively easier to clean and keep clean.

Figure 10:
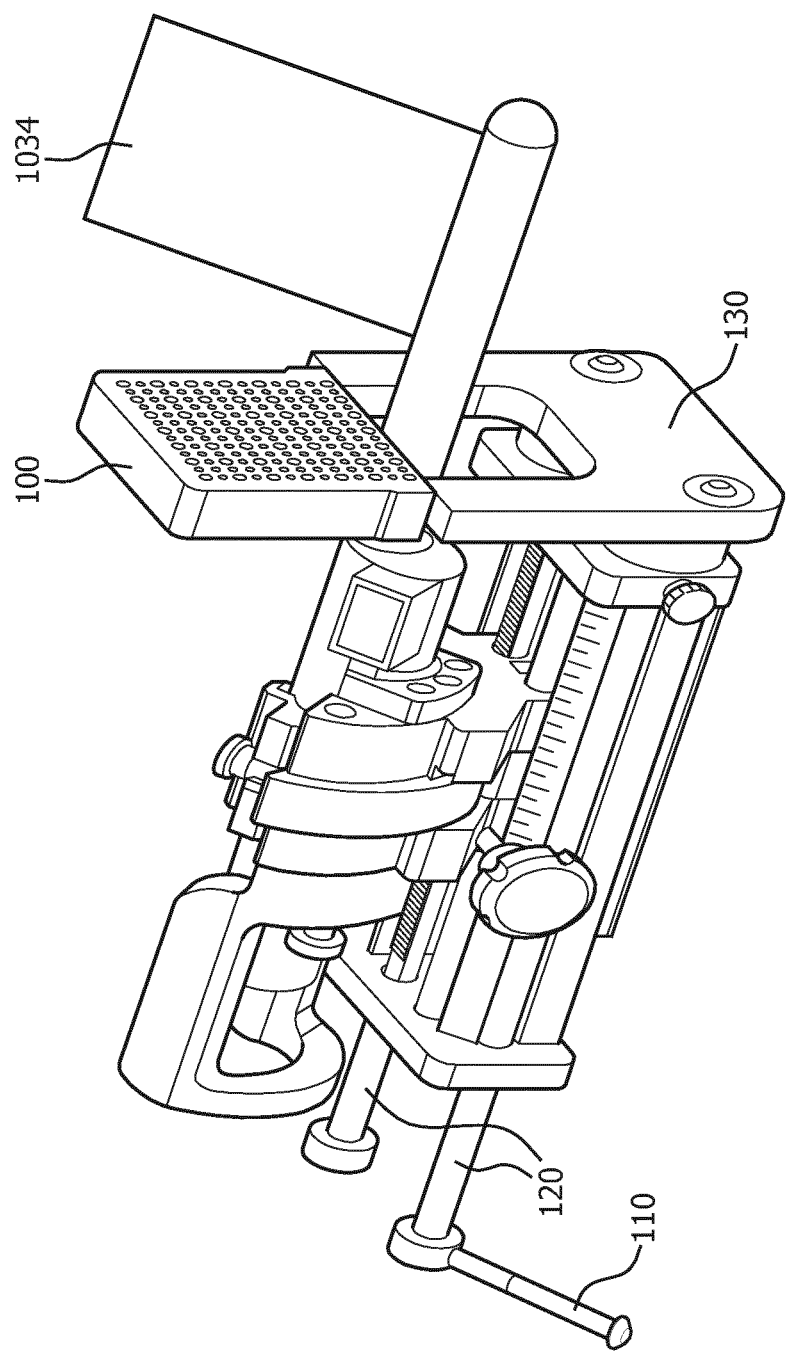
FIG. 10 is a perspective view showing a system for a tilt-controlled grid integrated to/with a conventional stepper, in accordance with a representative embodiment.

FIG. 10 is a perspective view showing a system for a tilt-controlled grid integrated to/with a conventional stepper, in accordance with a representative embodiment. In FIG. 10, the conventional stepper is integrated with the system for a tilt-controlled grid. Therefore, the levers 110 are at the rear, and the cams 120 run through the conventional stepper. A conventional stepper in FIG. 10 allows precision control of the tilt-controlled grid in the same manner as it would allow precision control of a conventional grid that only maneuvers vertically and horizontally. An ultrasound array 1034 may be positioned as shown in FIG. 10.

Figure 11:
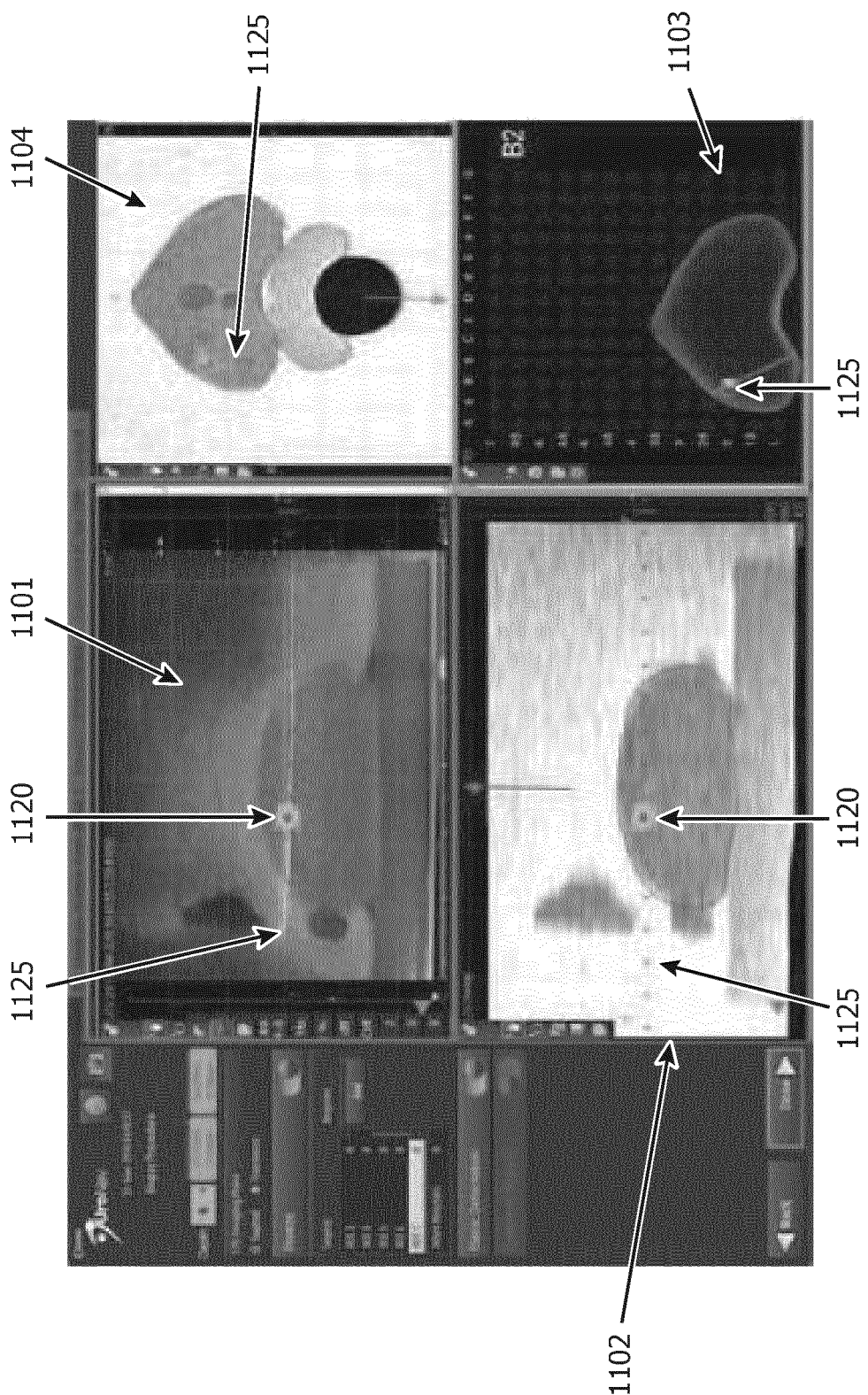
FIG. 11 is a view showing an image of a subject in a procedure involving a system for a tilt-controlled grid, in accordance with a representative embodiment.

FIG. 11 is a view showing an image of a subject in a procedure involving a system for a tilt-controlled grid, in accordance with a representative embodiment. In FIG. 11, four different images are displayed on a screen. To the upper left is an ultrasound stream image 1101. The target location 1120 is designated by arrows in the ultrasound stream image 1101 and in image 1102, interactive/targetable image 1103, and image 1104. The target location 1120 may be the location where a clinician wants to obtain a biopsy. The full grid plate 100 is shown in image 1103, and a horizontal line of dots is a dot trajectory 1125 for the needle in ultrasound stream image 1101.

The ultrasound stream image 1101 may result from ultrasound or a similar imaging arrangement used to produce views from electromagnetic tracking data. The views may be provided on a screen, similar to ultrasound images provided during pregnancy check-ups. The images can be used to align electromagnet tracking data and the actual physical characteristics of the subject of the ultrasound onto a common coordinate system. Using the aligned coordinates, a needle guided using the grid plate 100 can be guided using only the images, though a live video may help an operator ensure accuracy as the needle travels to the target.

The images in FIG. 11 may reflect tracking by a three-dimensional (3D) sensor that tracks movement of a needle, so that the movement can be displayed on the screen for an operator. The three-dimensional sensor may be an electromagnetic image, and the image may show whether the grid plate 100 is aligning with a subject who is undergoing a procedure. Alternatively, the images may be obtained from a camera that is positioned to capture an operation including positioning of the grid body 130.

Using the images in FIG. 11, an operator can watch as a needle is guided through the grid plate 100 into a subject. Although theoretically an operator could rely on ultrasound and MRI images without watching a live video, live videos used to produce images 1101, 1102, 1103, 1104 can help reassure an operator that a needle is being guided properly even though the operator is using precision machinery including the system for a tilt-controlled grid described herein. Images such as MRI images may be adapted to pre-existing generalized three dimensional models to produce detailed segmented models specific to a subject undergoing a procedure. An example of adapting a three-dimensional shape-constrained deformable brain model to structural MRI data from a subject to produce segmentation of a brain scan is described in, for example, U.S. Patent Application Publication No. 2015/0146951 to ZAGORCHEV et al, published on May 28, 2015, the entire contents of which are incorporated by reference herein.

Figure 12A:
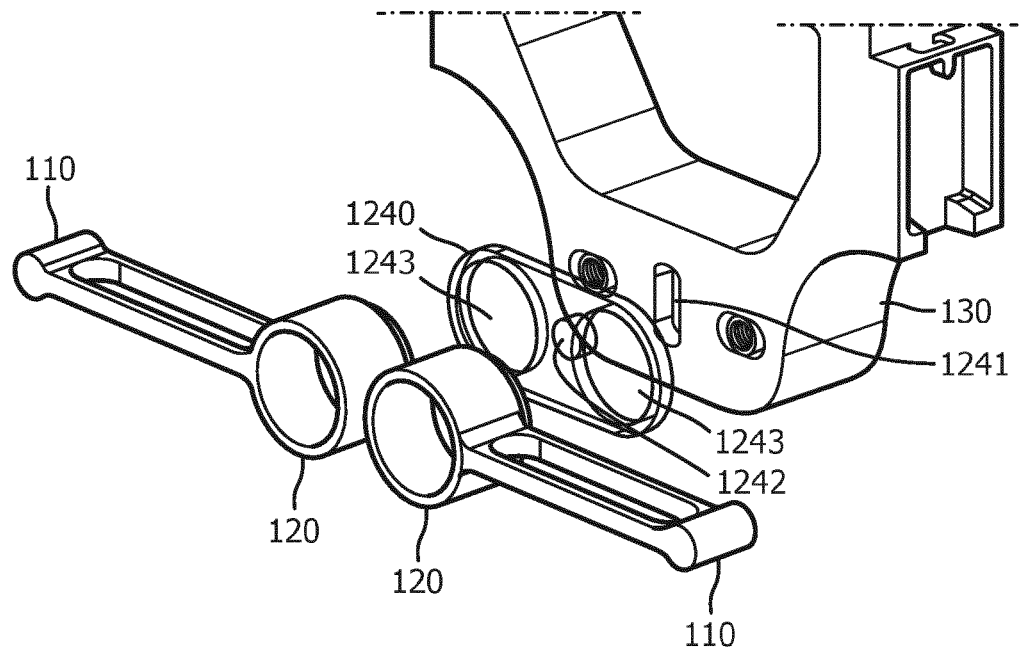
FIG. 12 A-C are views showing a system for a tilt-controlled grid, in accordance with a representative embodiment that includes a centralizer part.

FIGS. 12 A-C are views showing the apparatus in an embodiment which includes a centralizer part 1240. Because distances of the cams 120 change as they are used, one hole in a grid body 130 must have a slot 1241 which lets the cams 120 travel evenly as the distance changes. This causes a significant difficulty, when both lever arms are lifted at same time, the grid plate 100 travels not only vertically but horizontally as well. This may be very confusing for a user and make the apparatus more difficult to use. A centralizer part 1240 is an elongated plate with openings 1242 and 1243 as shown in FIG. 12A. The centralizer part 1240 can fix the distance of lever arms 110 and a pin or pins can be inserted in an opening 1242 of the centralizer part 1240 to centrally fix the grid body 130 and thereby the grid plate 100's horizontal movement but let the grid body 130 and grid plate 100 travel up-down and rotate. With this addition to the apparatus, when lever 110 arms are lifted at the same time, the grid plate 100 travels only vertically.

Figure 12B:
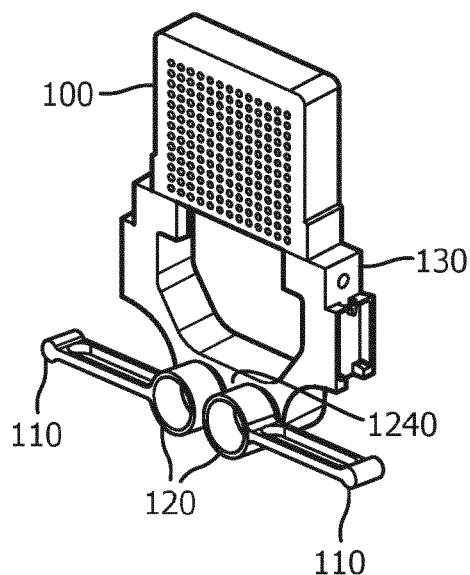
Figure 12C:
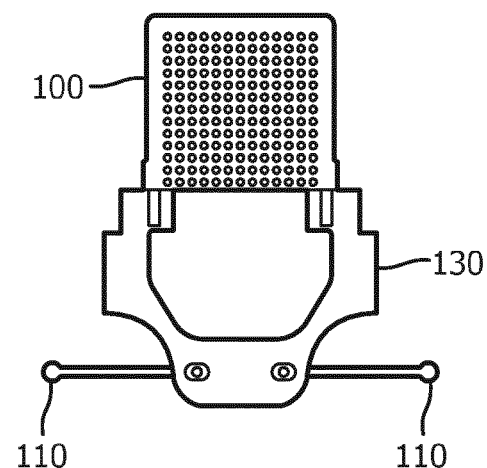

FIG. 12A is a perspective view of the levers 110, cams 120, centralizer part 1240, openings 1243 in the centralizer part 1240 to accommodate the cams 120, opening 1242 in the centralizer part 1240 for pin(s) to centrally fix the grid body 130 thereby fixing the grid plate 100's horizontal movement. The centralizer part 1240 is mounted between the cams 120 and the grid body 130. In the apparatus of FIG. 12A a single cam 120 may set both left and right movement of the grid body 130. A single pin may be used to replace the limiting pins 129 shown in FIG. 7. The ability of the apparatus to move the grid plate 100 vertically and to tilt the grid plate 100 to the left or right is not changed by the addition of the centralizer part 1240, but the grid body cannot move linearly left to right. FIG. 12B is a perspective view with the grid plate 100 in place. FIG. 12C is a back view of levers 110, grid body 130 and grid plate 100.

The system for a tilt-controlled grid shown herein may be manufactured entirely of, for example, plastic materials. Alternatively, the materials may include titanium. As a general matter, the system for a tilt-controlled grid should be made of appropriate materials for an environment that includes magnetic resonance imaging (MRI) equipment when the system for a tilt-controlled grid is used around MRI equipment.

The system for tilt-controlled grid is described herein in the context of transperineal procedures. However, many different medical applications use needle guides to drive medical needles to an intended location. The use of levers 110 as described herein provides room to an operator for finger adjustment. As a general matter, using the system for tilt-controlled grid described herein, linear X and Y movements are replaced by a grid plate 100 tilt movement. The system for tilt-controlled grid is actually a simpler design and allows for faster manipulations due to the relative placements of the levers 110 and cams 120.

As an example, the holes in a grid plate 100 may be 5 mm apart. As described, the use of levers 110 results in a diminished magnitude of movement between the relatively large movement of the levers 110 and the relatively small and precise movement of the grid plate 100. On the other hand, the use of imaging equipment such as ultrasound or MRI (or even a camera in an embodiment) allows for magnification of the movement in the images shown, for example, in FIG. 11. Thus, hand movements can be controlled to allow precise translations between the levers 110 and the grid plate 100, while the magnified imaging can be used to ensure that the operator has no trouble visualizing the area impacted by the needle in the procedure.

Further, the system for tilt-controlled grid may be provided without any screws that require turning by the operator. Instead, the levers 110 should be easily grasped and maneuvered.

The cams 120 may be cam wheels. In an embodiment, one cam 120 may be fixed such that only rotation is allowed, whereas the other cam 120 may be allowed to both rotate and slide linearly. Insofar as the distance between pegs 121, 122 on the cams 120 will vary when the levers 110 move, so one cam 120 is allowed to slide linearly in the z direction in order to ensure maneuverability of the levers 110.

Additionally, while the grid plate 100 is described herein as the needle guide, a needle guide manipulated by a system for tilt-controlled grid does not actually have to be a grid. For example, a needle guide may be provided with a single hole, or only a few holes that are not formed in a grid or array. That is, the system for tilt-controlled grid described herein can be provided independent of the grid plate 100, and even independent of the grid body 130. As a result, the system for tilt-controlled grid will be compatible with other forms of needle guides and other forms of similar medical equipment that requires precise maneuverability in the XY plane.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. An apparatus for controlling a needle guide, the apparatus comprising:
 a first lever;
 a second lever;
 a first cam attached to and extending from the first lever to a housing under the needle guide; and
 a second cam attached to and extending from the second lever to the housing under the needle guide,
 wherein at least one of the first cam and the second cam is configured to translate rotational movement from the respective first lever and the second lever to both linear and rotational movement of the needle guide via the housing.

2. The apparatus of claim 1, further comprising:
 a first device integrated with the first cam to convey the rotational movement from the first lever substantially horizontally to the housing; and
 a second device integrated with the second cam to convey the rotational movement from the second lever substantially horizontally to the housing.

3. The apparatus of claim 1, wherein the housing includes a first gear configured to translate rotational movement from the first cam to linear movement via the housing, the housing includes a second gear configured to translate rotational movement from the second cam to linear movement via the housing.

4. The apparatus of claim 1, wherein the needle guide comprises a grid plate, and when the first lever and the second lever are moved together, the grid plate moves substantially vertically.

5. The apparatus of claim 1, wherein the needle guide comprises a grid plate, and wherein when the first lever is moved and the second lever is maintained stationary, the grid plate is held in place about a pivot while being rotated about the pivot.

6. The apparatus of claim 1, wherein the rotational movement of the needle guide tilts the needle guide around an axis.

7. The apparatus of claim 6, wherein the axis is moved when at least one of the first cam and the second cam translates movement from at least one of the first lever and second lever to the linear movement of the needle guide via the housing.

8. The apparatus of claim 1, wherein the apparatus comprises a transperineal stepper.

9. The apparatus of claim 1, further comprising: the needle guide, wherein the needle guide comprises a grid plate.

10. The apparatus of claim 9, wherein the grid plate is guided by manipulating at least one of the first lever and second lever so that one of a plurality of holes in the grid plate is manipulated to align with a target location.

11. The apparatus of claim 1, wherein the first lever and the second lever are provided at a horizontal offset from the housing under the needle guide.

12. The apparatus of claim 1, wherein rotation of the first lever about a first axis by less than 180 degrees and rotation of the second lever about a second axis by less than 180 degrees produces vertical movement of the needle guide in a range less than 25 millimeters.

13. The apparatus of claim 1, wherein rotation of the first lever about a first axis while the second lever is maintained stationary holds the needle guide in place about a pivot while the needle guide is rotated about the pivot by the first lever.

14. The apparatus of claim 1, further comprising: an imaging device that captures data used to produce an image of a target location in real time.

15. The apparatus of claim 14, wherein movement of at least one of the first lever and the second lever about an axis is diminished in linear translation to the needle guide, and vertical and rotational movement of the needle guide is magnified in the image of the target location in real time.

16. The apparatus of claim 1, further comprising a centralizer part.

17. An apparatus for controlling a needle guide, the apparatus comprising:
 a housing under the needle guide;
 a first cam configured to translate rotational movement to linear movement via the housing, and comprising a first central axis therethrough and a first peg that directly contacts the housing;
 a second cam configured to translate rotational movement to linear movement via the housing, and comprising a second central axis therethrough and a second peg that directly contacts the housing;
 a first lever attached to the first cam at a horizontal offset from the housing and configured to rotate the first cam about the first central axis to convey the rotational movement of the first cam; and
 a second lever attached to the second cam at a horizontal offset from the housing and configured to rotate the second cam about the second central axis to convey the rotational movement of the second cam;
 wherein at least one of the first cam and the second cam is configured to translate rotational movement from the respective first lever and the second lever to both linear and rotational movement of the needle guide via the housing.

18. The apparatus of claim 17, wherein the first central axis and second central axis comprise parallel lines.

19. The apparatus of claim 17, wherein the first cam is fixed in place relative to the housing so as to be rotated by the first lever, and the second cam is linearly movable relative to the housing and configured to b rotated by the second lever.

20. The apparatus of claim 17, further comprising a centralizer part.

* * * * *